United States Patent
Heim et al.

(10) Patent No.: US 8,562,603 B2
(45) Date of Patent: Oct. 22, 2013

(54) METHOD FOR CONDUCTING ELECTROSURGERY WITH INCREASED CREST FACTOR

(75) Inventors: Warren P. Heim, Boulder, CO (US); James L. Brassell, Boulder, CO (US)

(73) Assignee: Microline Surgical, Inc., Beverly, MA (US)

( * ) Notice: Subject to any disclaimer, the term of this patent is extended or adjusted under 35 U.S.C. 154(b) by 1686 days.

(21) Appl. No.: 11/427,713

(22) Filed: Jun. 29, 2006

(65) Prior Publication Data

US 2007/0005060 A1   Jan. 4, 2007

Related U.S. Application Data

(60) Provisional application No. 60/695,692, filed on Jun. 30, 2005.

(51) Int. Cl.
*A61B 18/14* (2006.01)

(52) U.S. Cl.
USPC .............................................. 606/45; 606/41

(58) Field of Classification Search
USPC .............................. 606/37, 41, 45, 48, 49, 50
See application file for complete search history.

(56) References Cited

U.S. PATENT DOCUMENTS

| | | |
|---|---|---|
| 874,178 A | 12/1807 | DeForest |
| 1,713,970 A | 5/1929 | Lowrey et al. |
| 3,799,168 A | 3/1974 | Peters |
| 3,963,030 A * | 6/1976 | Newton .......................... 606/40 |
| 3,970,088 A | 7/1976 | Morrison |
| 3,987,795 A | 10/1976 | Morrison |
| 4,033,351 A | 7/1977 | Hetzel |
| 4,043,342 A | 8/1977 | Morrison, Jr. |
| 4,074,718 A | 2/1978 | Morrison, Jr. |
| 4,161,950 A | 7/1979 | Doss et al. |
| 4,202,337 A | 5/1980 | Hren et al. |
| 4,228,800 A | 10/1980 | Degler, Jr. et al. |
| 4,248,231 A | 2/1981 | Herczog et al. |
| 4,314,559 A | 2/1982 | Allen |

(Continued)

FOREIGN PATENT DOCUMENTS

| | | |
|---|---|---|
| EP | 1566645 | 8/2005 |
| WO | 94/28809 A1 | 12/1994 |

(Continued)

OTHER PUBLICATIONS

Serway, Raymond; Physics for Scientists and Engineers; Thomson Brooks/Cole, Belmont, CA; 2004; pp. 746-755.

(Continued)

*Primary Examiner* — Michael Peffley
*Assistant Examiner* — Samantha Good
(74) *Attorney, Agent, or Firm* — Greenblum & Bernstein, P.L.C.

(57) ABSTRACT

A method for conducting electrosurgery using increased crest factors employs an electrosurgical instrument having at least one conductive element that is surrounded by an insulation layer except at a conductor edge portion of the conductive element. The conductor edge portion and insulation layer each having unique geometric shapes and composition of the parts concentrate the electrosurgical power, reduce or eliminate the production of smoke and eschar and reduce tissue damage. The outer profile of the insulation layer and conductive element are configured to facilitate the flow of electrosurgical decomposition products away from the conductor edge where they are formed. The combined effects of the electrosurgical instrument configurations enable safe use of crest factors of 5 or greater in electrosurgical procedures.

8 Claims, 9 Drawing Sheets

(56) References Cited

U.S. PATENT DOCUMENTS

| | | | |
|---|---|---|---|
| 4,333,467 A | 6/1982 | Domicone | |
| 4,449,926 A | 5/1984 | Weiss | |
| 4,481,057 A | 11/1984 | Beard | |
| 4,492,231 A | 1/1985 | Auth | |
| 4,534,347 A | 8/1985 | Taylor | |
| 4,545,375 A | 10/1985 | Cline | |
| 4,565,200 A | 1/1986 | Cosman | |
| 4,589,411 A | 5/1986 | Friedman | |
| 4,622,966 A | 11/1986 | Beard | |
| 4,657,016 A | 4/1987 | Garito et al. | |
| 4,785,807 A | 11/1988 | Blanch | |
| 4,793,346 A | 12/1988 | Mindich | |
| 4,823,791 A | 4/1989 | D'Amelio et al. | |
| 4,848,337 A | 7/1989 | Shaw et al. | |
| 4,931,047 A | 6/1990 | Broadwin et al. | |
| 4,976,711 A | 12/1990 | Parins et al. | |
| 5,015,227 A | 5/1991 | Broadwin et al. | |
| 5,030,218 A | 7/1991 | Alexander | |
| 5,080,660 A | 1/1992 | Buelna | |
| 5,160,334 A | 11/1992 | Billings et al. | |
| 5,167,659 A | 12/1992 | Ohtomo et al. | |
| 5,267,994 A | 12/1993 | Gentelia et al. | |
| 5,308,311 A | 5/1994 | Eggers et al. | |
| 5,318,562 A | 6/1994 | Levy et al. | |
| 5,318,563 A | 6/1994 | Malis et al. | |
| 5,370,645 A | 12/1994 | Klicek et al. | |
| 5,380,320 A | 1/1995 | Morris | |
| 5,382,247 A | 1/1995 | Cimino et al. | |
| 5,423,810 A * | 6/1995 | Goble et al. | 606/40 |
| 5,464,390 A | 11/1995 | Arnett et al. | |
| 5,472,442 A | 12/1995 | Klicek | |
| 5,472,443 A | 12/1995 | Cordis et al. | |
| 5,520,684 A | 5/1996 | Imran | |
| 5,540,681 A | 7/1996 | Strul et al. | |
| 5,549,604 A | 8/1996 | Sutcu | |
| 5,554,172 A | 9/1996 | Horner et al. | |
| 5,633,578 A | 5/1997 | Eggers et al. | |
| 5,643,256 A | 7/1997 | Urueta | |
| 5,693,045 A | 12/1997 | Eggers et al. | |
| 5,693,060 A | 12/1997 | Martin | |
| 5,697,909 A | 12/1997 | Eggers et al. | |
| 5,697,926 A | 12/1997 | Weaver | |
| 5,702,387 A | 12/1997 | Arts et al. | |
| 5,707,402 A | 1/1998 | Heim | |
| 5,713,895 A | 2/1998 | Lontine et al. | |
| 5,766,153 A | 6/1998 | Eggers et al. | |
| 5,833,686 A | 11/1998 | Zhao | |
| 5,836,943 A | 11/1998 | Miller | |
| 5,891,095 A | 4/1999 | Eggers et al. | |
| 6,030,218 A | 2/2000 | Robinson | |
| 6,039,735 A | 3/2000 | Greep | |
| 6,059,783 A | 5/2000 | Kirwan | |
| 6,066,137 A | 5/2000 | Greep | |
| 6,074,387 A | 6/2000 | Heim et al. | |
| 6,106,519 A | 8/2000 | Long et al. | |
| 6,132,427 A | 10/2000 | Jones et al. | |
| 6,228,081 B1 | 5/2001 | Goble | |
| 6,235,020 B1 | 5/2001 | Cheng et al. | |
| 6,238,387 B1 | 5/2001 | Miller | |
| 6,241,723 B1 | 6/2001 | Heim et al. | |
| 6,287,305 B1 | 9/2001 | Heim et al. | |
| 6,312,428 B1 * | 11/2001 | Eggers et al. | 606/41 |
| 6,413,255 B1 | 7/2002 | Stern | |
| 6,533,781 B2 * | 3/2003 | Heim et al. | 606/45 |
| 6,673,069 B1 * | 1/2004 | Hood | 606/41 |
| 6,685,704 B2 | 2/2004 | Greep | |
| 6,692,489 B1 | 2/2004 | Heim et al. | |
| 6,758,846 B2 | 7/2004 | Goble et al. | |
| 2003/0073993 A1 * | 4/2003 | Ciarrocca | 606/41 |
| 2003/0109864 A1 | 6/2003 | Greep et al. | |
| 2003/0114848 A1 * | 6/2003 | Cobb | 606/48 |
| 2003/0158545 A1 * | 8/2003 | Hovda et al. | 606/32 |
| 2003/0220638 A1 | 11/2003 | Metzger | |
| 2004/0116919 A1 | 6/2004 | Heim et al. | |
| 2004/0147922 A1 * | 7/2004 | Keppel | 606/41 |
| 2005/0143725 A1 | 6/2005 | Daners et al. | |
| 2005/0154385 A1 | 7/2005 | Heim et al. | |
| 2006/0025757 A1 | 2/2006 | Heim | |

FOREIGN PATENT DOCUMENTS

| | | |
|---|---|---|
| WO | 96/34571 A1 | 11/1996 |
| WO | 97/11649 A1 | 4/1997 |
| WO | 98/47436 A1 | 4/1998 |
| WO | WO9940858 * | 2/1999 |
| WO | 9940858 A1 | 8/1999 |
| WO | 02/28301 | 4/2002 |
| WO | 03/090635 | 11/2003 |
| WO | 2005046739 A2 | 5/2005 |
| WO | 2006031289 A2 | 3/2006 |

OTHER PUBLICATIONS

"Coated Electrode Technology . . . ", 2006; ValleyLab, Boulder, Colorado.
"MEGADYNE—Stainless Steel Electrodes"; http://www.megadyne.cor/sstips.hlrn; Jun. 1, 2002; MEGADYNE Medical Products, Inc., Draper, Utah.
English language Abstract of WO 02/28301, Apr. 11, 2002.
PCT/US2005/025681 International Preliminary Report on Patentability and Written Opinion, Feb. 22, 2007.
PCT/US2005/025681 International Search Report and Written Opinion, Jan. 24, 2007.
PCT/US06/25123 International Search Report and Written Opinion, Jan. 3, 2007.
PCT/US06126122 International Search Report and Written Opinion, Jan. 25, 2007.

* cited by examiner

METHOD FOR CONDUCTING ELECTROSURGERY WITH INCREASED CREST FACTOR

This application claims the benefit of priority to U.S. Provisional Application 60/695,692 entitled Multielectrode Electrosurgical Instrument filed Jun. 30, 2005, the entire contents of which are hereby incorporated by reference.

FIELD OF THE INVENTION

The present invention relates to surgical methods and apparatus, and more particularly to applying electrosurgical power to a tissue site to achieve a predetermined surgical effect.

BACKGROUND OF THE INVENTION

The potential applications and recognized advantages of employing electrical energy in surgical procedures continue to increase. In particular, for example, electrosurgical techniques are now being widely employed to provide significant localized surgical advantages in open, laparoscopic, and arthroscopic applications, relative to surgical approaches that use mechanical cutting such as scalpels.

Electrosurgical techniques typically entail the use of a hand-held instrument that contains one or more electrically conductive elements that transfer alternating current electrical power operating at radio frequency (RF) to tissue at the surgical site, a source of RF electrical power, and an electrical return path device, commonly in the form of a return electrode pad attached to the patient away from the surgical site (i.e., a monopolar system configuration) or a return electrode positionable in bodily contact at or immediately adjacent to the surgical site (i.e., a bipolar system configuration). The time-varying voltage produced by the RF electrical power source yields a predetermined electrosurgical effect, such as tissue cutting or coagulation.

During electrosurgical procedures electric current flows through one or more conductive elements, the active electrodes, and transfers electrical current to tissues, often with coincident sparks or arcs of electricity occurring between one or more electrodes and tissues. The overall process causes heating of tissue and the electrode metal. Tissue heating causes tissues to break into fragments or otherwise change into materials that generally differ physically and chemically from the tissue before it was affected by electrosurgery. The tissue changes at the surgical site, such as charring, interfere with normal metabolic processes and, for example, kill tissues that remain at the surface of incisions. The changes in tissues caused by electrosurgical energy, such as killing parts of tissues, are known to interfere with healing at the surgical site.

Beyond damaging tissue at the surgical site, conventional electrosurgery has other drawbacks which limit its applicability or increase the costs and duration of procedures. Induced heating of tissues and electrodes causes smoke plumes to issue from the tissue. Smoke obscures the field of view and hinders surgical procedures and is also a known health hazard. Controlling smoke once it has formed is problematic, requiring the evacuation of large volumes of air in order to capture an appreciable fraction of the smoke with wands that are close to the surgical site where they are in the way, and adds costs in both additional equipment and labor.

The induced heating also generally causes tissue that has been altered by electrosurgery to adhere to and partially coat electrosurgical electrodes. The tissue fragments that adhere to electrodes and coat the electrodes is called "eschar." The coatings on blades that form from tissue and tissue fragments are typically rich in carbon and contain various compounds that tend to make the coatings electrically conductive when energized by the type of power used for electrosurgical procedures. Eschar inhibits the effectiveness of electrosurgical devices and must frequently be removed, hindering surgical procedures.

Despite advances in the field, electrosurgical blades continue to suffer from one or more of the problems of producing smoke, having materials from tissues coat the blades, and damaging tissue. Therefore, a need exists to improve performance in each of these areas. Historically, electrosurgical blades have generally not given consideration to the chemical reaction environment and conditions that occur where the electrosurgical energy interacts with tissue by considering factors such as the propensity of tissue to become trapped in regions that lead to prolonged residence times at reactive conditions that lead to producing smoke and materials that coat blades to form eschar. Likewise, prior art electrosurgical blades did not consider the conductive pathways that can be formed by tissue fragments adhering to blades and the effects that these built-up conductive pathways have on producing smoke, producing more materials that can further coat blades, and the effects that these have during electrosurgery.

The aforementioned limitations in conventional electrosurgery impose limits on the peak voltage that can be applied to tissue during electrosurgery.

SUMMARY

Various embodiments provide a method for conducting electrosurgery with higher crest factors, which is the ratio of the peak voltage to the root mean square (RMS) voltage applied to tissue. By increasing the safe and effective crest factor, enhanced therapeutic effects are enabled.

The various embodiments use electrosurgical instruments having a blade geometry, blade composition or a combination of blade geometry and composition that concentrates electrosurgical energy and reduces or prevents smoke production, eschar accumulations, and/or tissue damage. The embodiment instruments focus electrosurgical energy to a small amount of tissue for a short duration compared to the amount of tissue and duration than is customary during electrosurgery using conventional technology. Various embodiments yield less eschar accumulation on the electrosurgical instrument by providing an exterior surface of the instrument with a shape that facilitates movement of tissue decomposition products away from the active region of the conductive element. The active region is a region on the conductive element where electrosurgical energy transfers from the blade to tissue. In some embodiments, the tapered configuration includes an electrically conductive element with a tapered section. In some embodiments, the tapered configuration includes configuring an insulating layer with a tapered section. In various embodiments, insulation on the conductive element has a surface free energy that reduces the propensity for electrosurgical decomposition products (defined herein) to stick to the surface. In various embodiments, the shape of the blade minimizes the duration that the active region is near any particular portion of tissue as the blade is moved through tissue as during an incision.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain features of the invention.

DETAILED DESCRIPTION OF THE PREFERRED EMBODIMENT

Figure 1:
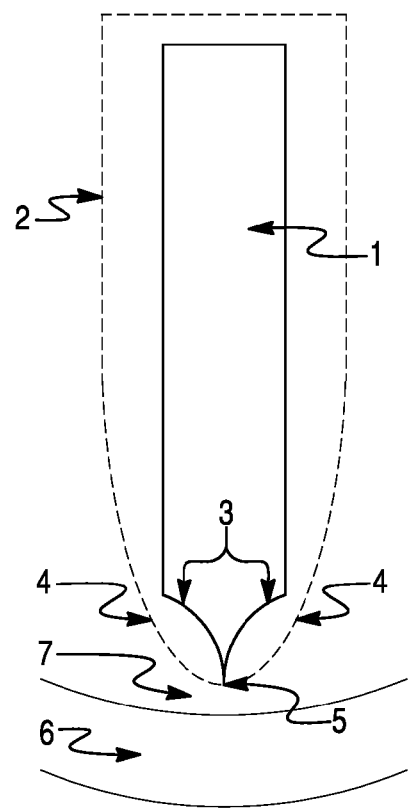
FIG. 1 portrays a cross-section of a blade that has been insulated whereby the outer taper to the edge is defined by a single smooth curve at the conductor edge.

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient", "tissue" and "subject" refer to any human or animal subject and are not intended to limit the systems or methods to human use, although use of the subject invention on a human patient represents a specific embodiment.

All devices that may be used to produce a predetermined surgical effect by applying RF power to tissue may be referred to herein as electrosurgical "blades" due to their function of partial or complete removal of one or more parts of tissue (including changing the structure such as by at least partially denaturing or decomposing), regardless of their size, shape, or other properties. Use of the term "blade" herein is not intended to restrict the description or any embodiment to a particular shape or configuration. While various embodiments pertain to generally planar elements which may resemble a conventional scalpel blade, other embodiments encompass element configurations which are dissimilar from conventional blades, including, for example, needle, hook and curved configurations.

Reference herein to the purpose and effects of electrosurgical devices as producing "a predetermined surgical effect" encompasses all potential effects generated during electrosurgery. The predetermined surgical effect include, but are not limited to: causing a partial or complete separation of one or more tissue structures or types, including, but not limited to making electrosurgical incisions; cause partial or complete removal of one or more parts of a tissue; changing the structure of tissue, such by at least partially denaturing or decomposing tissue; cutting; hemostasis (such as by inducing coagulation); tissue welding; tissue sealing, and tissue shrinking. Commonly, multiple predetermined surgical effects occur simultaneously, such as cutting and hemostasis both occurring as incisions are made.

Although they may have various forms, all sources of RF power used to power electrosurgical blades will be referred to herein as electrosurgical units and abbreviated by ESU.

The terms "electrode" and "conductive elements" are used interchangeably herein to refer to similar structures without intending to communicate or imply a difference in structure or limitation on any embodiment or claim of the present invention.

Electrosurgical devices come in two common varieties, monopolar and bipolar. Monopolar electrosurgical blades connect to an ESU using a wire while a separate return pad is connected to the ESU by another wire. Bipolar electrosurgical blades connect a set of one or more active electrodes to the ESU with one or more wires and connect another set of one or more return electrodes to the ESU with one or more other wires, wherein the active electrode or electrodes and return electrodes or electrode are connected together so that RF energy may be conveyed through one or more conductive media that contact at least one tissue with such connections between electrodes being either permanent or temporary, such as by being separately inserted into a clamping device or a handle with such connection being fixed or moveable, such as a sliding connection.

The present inventors have recognized that reducing the amount of energy applied to tissue reduces tissue breakdown and that the amount of applied energy can be reduced by reducing the exposure to electrosurgical power (where electrosurgical power is the rate at which electrosurgical energy is applied) either by reducing the power level, the time of exposure to electrosurgical power, or by reducing both the power level and the time of exposure. Various embodiments reduce the amount of energy to which tissue is exposed by proper selection of blade geometry, blade materials, and the amount of power used.

More generally in this regard, energy discharge from electrosurgical instruments may be in the form of electrical energy and/or thermal energy. Electrical energy is transferred whenever the electrical resistance of a region between an electrosurgical instrument and tissue can be broken down by the voltage of the electrosurgical power. Thermal energy is transferred when thermal energy that has accumulated in the electrosurgical instrument overcomes the thermal resistance between the instrument and the tissue (i.e. due to temperature differences therebetween) and is transferred to tissue by conduction, radiation and/or convection. Transferring electrosurgical energy to tissue occurs at portions of the electrosurgical instrument which cause the desired surgical effect, such as forming an incision. Such portions of the instrument are called functional areas. All other portions of the electrosurgical instrument are nonfunctional, and transfer of electrosurgical energy to tissue from these portions should be minimized. Electrosurgical energy may be transferred to tissue without direct contact with the functional area by means of electrical sparks and radiative and convective heat transfer. As used herein, the term "contact" relating to the position of blades or electrodes near tissue encompasses both actual contact and positioning of a functional area close enough to tissue for transfer of electrosurgical energy to occur.

Pyrolysis is the breakdown of molecules into smaller moieties by the action of heat (physical fragmentation), typically followed by subsequent recombination of these thermal fragments to form larger species. As used herein, the term "electropyrolysis" refers to the process whereby electrical energy in the form of sparks or arcs interacts with tissue to break down tissue constituents by heat, electron interactions with materials, photon interactions with materials, or any combination of these.

In general terms, electrosurgery is the process by which high voltage (e.g., voltages greater than about 100 volts) electrical power is applied to tissue to achieve a predetermined surgical effect. Such voltages are typically employed as high frequency (e.g., frequencies greater than about 5 kHz) and most commonly use frequencies greater than about 100 kHz to reduce neuromuscular stimulation. The energy is transferred to tissue at the surgical site using one or more electrodes. Electrical energy is transferred as well as thermal energy which comes from electrodes becoming hot as electrical power moves through them, producing $I^2R$ power losses which manifest themselves as heat, some of which is transferred to tissue via conduction, radiation, and convection. As used herein, the term "electrosurgical energy" refers to all of the energy transferred to tissue during electrosurgery, regardless of form or transfer mechanism, and including both electrical and thermal energy.

Without restriction to any particular theory of operation regarding its form or method of use, the following descriptions of processes during electrosurgery are provided to illustrate one or more candidate processes that could be present during electrosurgery to facilitate subsequent descriptions of the various embodiments.

Tissue breaks down where sparks or hot metal contact it. This breakdown of tissue is believed to be caused by rapid heating of tissue where electrosurgical energy, principally electrical sparks and thermal energy from hot metal, contacts tissue and electropyrolysis and hydrolysis lyse tissue constituents.

During electrosurgery a variety of reaction products are produced. Electropyrolysis is believed to be a cause of tissue breakdown during electrosurgery. One result of electropyrolysis during electrosurgery is the production of hot water and steam which promote hydrolysis of tissues. For example, electropyrolysis and hydrolysis are believed to break down proteins and produce a range of products, including cyclic and linear polypeptide materials. Electropyrolysis is also believed to be the process by which electrosurgery is able to cut or otherwise break down tissues that have a cellular structure (e.g., muscle tissue) as well as tissues that do not have a cellular structure (e.g., collagen fibrils in ligaments).

Beyond electropyrolysis products, other electrosurgery products are also formed. Most notable are changes in state in which materials change their state (e.g., steam forming when water changes from liquid to gas) but are otherwise not changed chemically. During electrosurgery some products have altered structure, but otherwise retain their chemical identity, such as when proteins denature and then refold into shapes different from those prior to denaturation. During electrosurgery some products retain their chemical structure and state, but change physically in other ways (e.g., air being heated so that its specific volume increases).

Finally, some electrosurgery processes can cause materials, such as cellular contents or viral particles, to be liberated or moved with a stream of other materials, such as being conveyed by flowing steam or hot air produced during electrosurgery.

Collectively, all of the materials produced or altered during electrosurgery, including those from electropyrolysis, change of state, change of structure, change of volume, and liberation are referred to herein as the "products of electrosurgery," "electrosurgical decomposition products," or "electrosurgical products". The collection of processes that break down or alter tissues during electrosurgery are referred to here as electrosurgical tissue decomposition processes.

Some of the resulting materials form smoke or steam and some of the resulting materials form substances that stick to blades. When electrosurgery is performed in a gaseous environment, such as air or carbon dioxide, particularly when incisions are made, a common result using conventional technology is a smoke plume. The smoke plume is believed to consist primarily of pyrolysis and electropyrolysis products, including steam and hot air along with materials such as cellular contents and other entrained materials.

When electrosurgery is performed, including when incisions are made, some of the products of electrosurgery form deposits on electrodes contacting or in close proximity to tissue. These deposits, called eschar, are believed to begin forming when sticky materials, such as denatured proteins, adhere to electrode surfaces. Other materials may also be mixed in with the sticky materials. As electrosurgery proceeds, thermal energy continues to pyrolyze these materials on the electrodes leading to the production of substances having a higher carbon:hydrogen content than the starting materials. Some resulting materials conduct electricity at the voltages used, perhaps due to the presence of ions from salts or by having high carbon contents, and form an electrically conductive coating on the blade, even if the blade's surface is coated with an insulating coating. Therefore, eschar formation on the outside of an insulated electrode that has, for example, only an edge exposed, can have an electrically active area that extends from the exposed edge because of conductive eschar deposits forming on the blade's surface and being in electrical contact with the exposed edge. This conductive deposit can expose more tissue to prolonged exposure to electrical energy.

The amount of electrosurgical products produced depends upon the amount of energy applied to tissue, the rate at which the energy is applied, and the length of time that tissue is exposed to sources of the energy. While conventional electrosurgical systems have attempted to control these factors by means of ESU settings, the present inventors have recognized that the configuration of electrosurgical blades also affect the time and amount of energy applied to portions of tissue, and thus to the generation of electrosurgical products. For example rough blade functional surfaces tend to retain tissue fragments and thus expose such tissue fragments to electrosurgical energy for longer durations than occurs when the blade has smooth functional surfaces. If recesses or pockets exist where material can be held in place in close proximity to the functional surfaces, the residence time for chemical reactions to occur increases for trapped materials. With increased residence time, more lysis occurs, leading to increased smoke and eschar production. As low molecular weight materials are lysed from trapped materials they leave as smoke and gases that are relatively rich in hydrogen, leaving behind an increasingly carbon-rich material. This material is eschar. When deposited on the surface of an insulating layer it effectively widens the electrically conductive edge, which exposes more tissue to electrosurgical energy and increases the time at which tissue is exposed to lysing conditions. Exposing more tissue to lysing conditions and exposing tissue for longer periods to such conditions causes more smoke and eschar to form, and thus it is desirable to prevent or reduce the occurrence of such conditions.

Using cutting as an example electrosurgical process, the power settings typically used during electrosurgery employing conventional electrosurgical systems are over 30 Watts, and often are on the order of 40 to 100 Watts. Theoretically, the amount of power required for cutting is much lower, between about 2 and 15 Watts. The surplus power beyond that theoretically required drives unwanted reactions such as the production of smoke and eschar as well as overheating tissue that kills cells.

Figure 4:
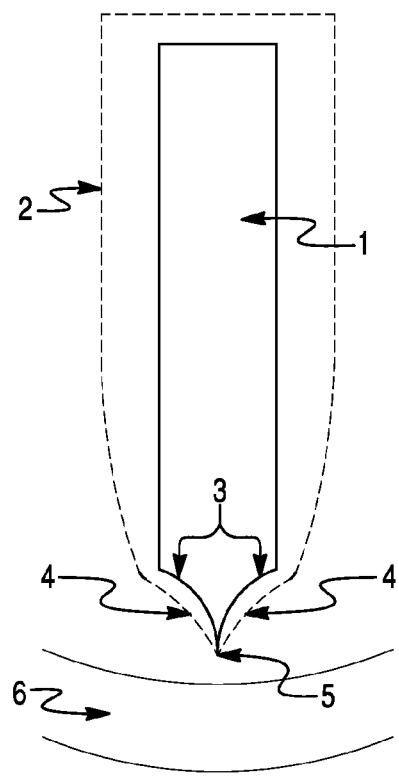
FIG. 4 portrays a cross-section of a blade with a conductive element that has a concave taper that has been insulated whereby the outer taper to the edge is not defined by a single smooth curve at the conductor edge.
Figure 5:
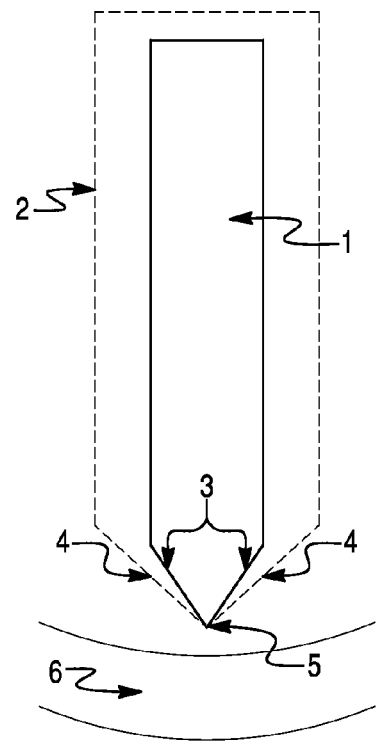
FIG. 5 portrays a cross-section of a blade with a conductive element that has a substantially flat taper that has been insulated whereby the outer taper to the edge is not defined by a single smooth curve at the conductor edge.

The various embodiments employ blade geometry, blade composition or a combination of blade geometry and composition to reduce or prevent smoke production, eschar accumulations, or tissue damage. The embodiments focus electrosurgical energy to a small amount of tissue for a short duration compared to the amount of tissue and duration than is customary during electrosurgery using conventional technology. In the embodiments, the electrosurgical energy flows from a conductive element that is surrounded by insulation except for an exposed edge or point. Providing a relatively small exposed edge or point on the conductive element restricts RF energy flow to this portion of the conductive element, minimizing energy transfer from the rest of the conductive element which is covered by insulation. In some embodiments, the exposed edge on the conductive element can be formed by tapering down the insulation covering from its thickness at the wide part of the conductive element to minimal thickness adjacent to the exposed edge, as illustrated in FIGS. 4 and 5. In other embodiments, the conductive element geometry ends in a point that is not covered by insulation, as also illustrated in FIGS. 4 and 5.

Various embodiments comprise electrosurgical instruments that use blade shape and composition to reduce the production of smoke and eschar by, among other methods, reducing the time that materials are exposed to electrosurgical energy. The result is reduced smoke production, reduced eschar production, and reduced tissue damage.

Various embodiments include electrosurgical instrument features that promotes the free flow of electrosurgical decomposition products such as steam, gases, and vapors away from regions near the functional surfaces where electrosurgical energy interacts with tissue and such gaseous decomposition products form. It is believed that facilitating the flow of gaseous decomposition products away from the functional surfaces where they are generated reduces the local gas pressure in the vicinity of the functional surfaces which would otherwise rise with the buildup of gaseous products. By reducing the pressure and promoting the flow of electrosurgical decomposition products, the conditions which cause pyrolysis and electropyrolysis of tissue and electrosurgical products are reduced, particularly in the vicinity of the functional surface just removed from where the desired electrosurgical effect occurs. It is believed that continued pyrolysis and electropyrolysis of electrosurgical decomposition products leads to more generation of smoke and eschar. Thus, by reducing pressure, and thus temperatures, in the vicinity of the functional surfaces and facilitating the escape of electrosurgical decomposition products, generation of smoke and eschar can be substantially reduced.

Figure 2:
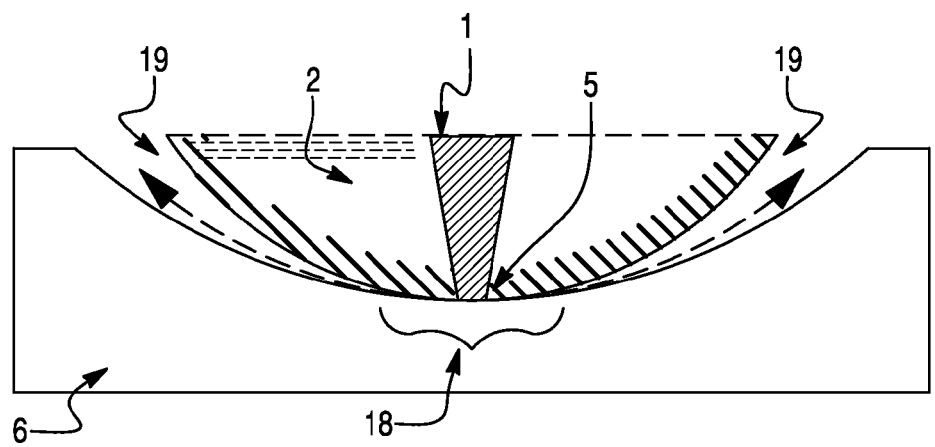
FIG. 2 portrays a magnified section of the region where electrosurgical energy interacts with tissue for the blade illustrated in FIG. 1.
Figure 14:
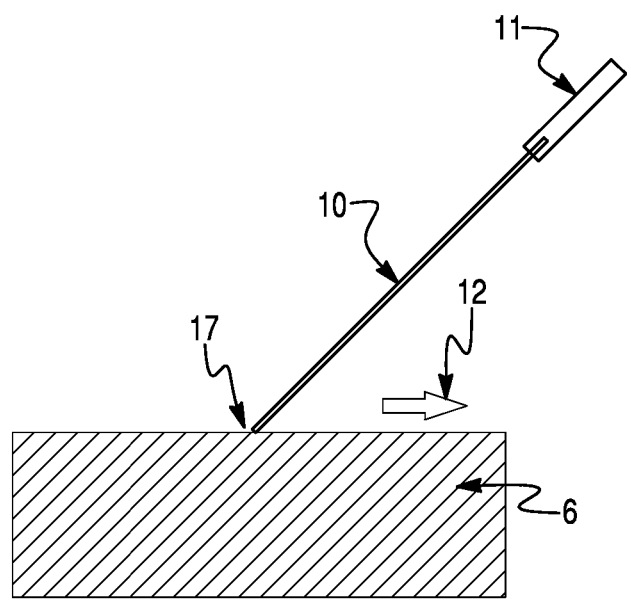
FIG. 14 portrays a side view of a needle electrode in relation to tissue.

In various embodiments, the electrosurgical instrument or blade features a narrow surface, edge or point in the vicinity of the functional area that reduces the length of the path that gases or vapors must traverse from the point of generation to reach ambient conditions, thus the distance and time during which decomposition products are exposed to high temperatures. In such embodiments, examples of which are illustrated in FIGS. 4-9, the functional surface is an edge of the blade that has at least one dimension (such as thickness) which is less than the corresponding dimension (such as thickness) of nonfunctional surfaces. In various embodiments, the edge or point is comprised of a metal conductor that is surrounded by insulation except for a section where the metal is exposed. In such embodiments, the outer profile of the insulation where the metal conductor is exposed is thinner than the outer profile at a distance removed from the exposed surface. In an embodiment, the edge or point is shaped so that it forms an acute angle where it comes in close contact with tissue during use. This aspect of the embodiments reduces the local gas pressure compared to, for example, a blade that has a relatively flat surface shape adjacent to the functional surface, such as when the combination of the insulation and conductive element form a round or parabolic profile, such as illustrated in FIGS. 1 and 2. In some embodiments, the edge is formed by tapering the profile so that the radial dimension at the functional surface is less than the radius of part of the nonfunctional surface of the blade. This configuration is not limited to planar blades and in an embodiment is employed in an electrosurgical instrument having a generally circular cross section, a configuration that is most commonly referred to as a needle electrode, such as illustrated in FIG. 14.

Figure 10:
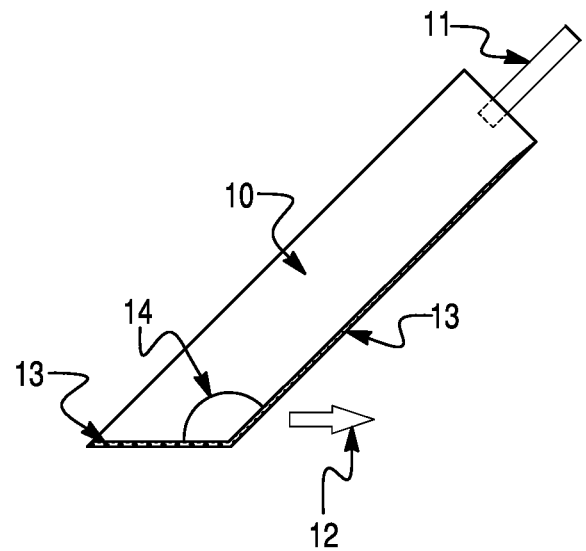
FIG. 10 portrays a side view of a blade with two exposed edges at an obtuse angle.
Figure 11:
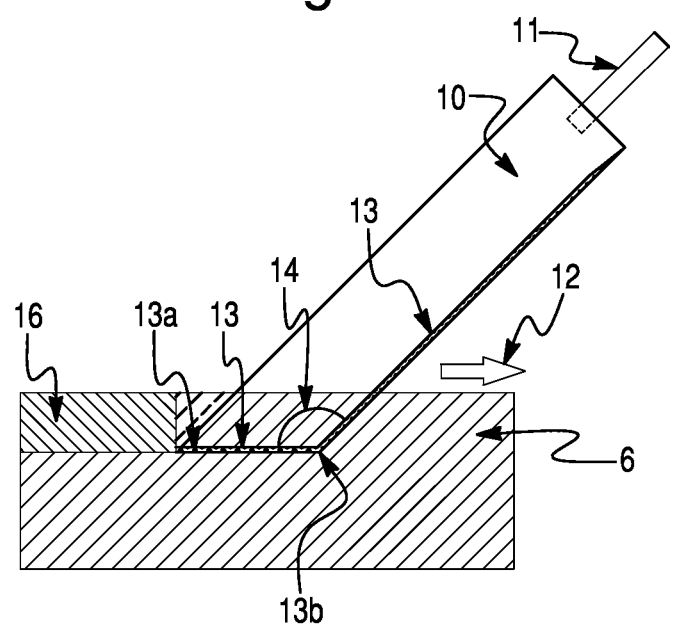
FIG. 11 portrays a side view of blade with two exposed edges at an obtuse angle in relation to making a tissue incision.
Figure 13:
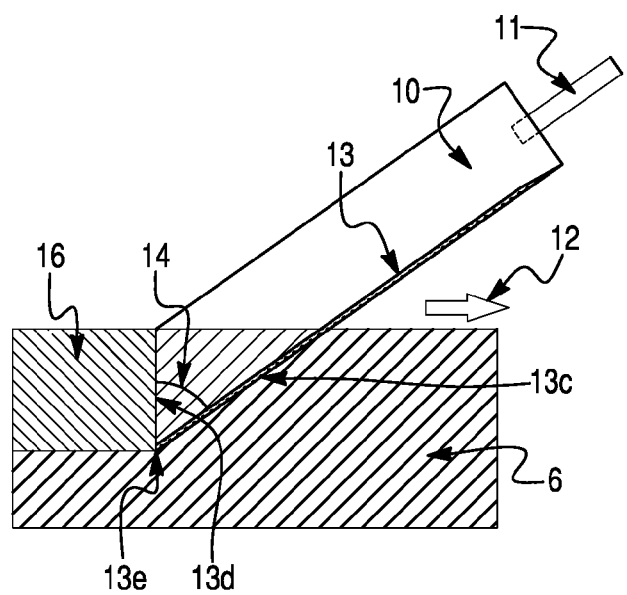
FIG. 13 portrays a side view of blade with one exposed edge in relation to making a tissue incision.

In other embodiments, the shape of the blade is configured such that when it contacts tissue and is moved through tissue, the amount of time that a tissue surface is adjacent to the functional surface is reduced or minimized. In some embodiments, the shape of the blade is configured such that it substantially has only a single line or point of contact of the functional surface with tissue. Such embodiments differ from conventional electrosurgical blades which typically allow electrosurgical energy to flow into tissue from both the edge and the sides of the blade. Some embodiments, an example of which is illustrated in FIG. 13, also differ from conventional blades that have two edges that are substantially not collinear, such as come to a form a 120 degree angle as illustrated in FIG. 10, such that one of the edges could be held approximately parallel to the tissue during use. Conventional blades of this configuration allow the same section of tissue to be exposed to electrosurgical energy over the entire time that the parallel section contacts the section of tissue, as illustrated in FIG. 11.

In various embodiments, the electrodes have functional surfaces in which the conductive elements are strictly convex in shape and thus do not contain recesses. Strictly convex surfaces do not have recesses in which tissue or electrosurgical decomposition products may become trapped. If tissue or electrosurgical decomposition products becomes momentarily trapped in a recess, such materials are exposed to electrosurgical energy and high temperature for a longer time, leading to generation of smoke and eschar. Such embodiments differ from conventional blades which have a nonconvex surface of the outer insulating surface where it extends to the edge of a metal electrode leaving the electrode slightly recessed into the insulation.

In various embodiments, the blade includes an outer insulating layer made of one or more materials selected to reduce thermal/electrical discharge from non-functional portions of the electrodes. In an embodiment, such an insulating layer surrounds at least a portion of bipolar electrodes. In various embodiments, the outer insulating layer has a thermal conductance of about 1.2 W/cm2 ° K and a dielectric withstand strength of at least about 50 volts. Such an insulating layer may advantageously comprise one or more materials with pores that have been sealed on the exterior surface to prevent biological materials from entering the pores. In an embodiment, such sealing material may contain one or more of various silicate materials or materials that form silicates. In an embodiment, at least part of the outer insulating layer or the substance bonding at least one pair of electrodes may comprise one or more materials that include one or more silicate materials and one or more hydrolysable materials that in combination form a thermally insulative substance that by itself is essentially hydrophobic and does not allow biologic material to penetrate its surface.

In various embodiments, one or more of the electrodes are metal with the electrodes having a thermal conductivity of at least about 0.35 W/cm ° K. Such electrode metals may comprise a metal selected from the group: gold, silver, aluminum, copper, tantalum, tungsten, columbium, and molybdenum, and alloys thereof. In various embodiments, one or more of the electrodes may be coated or plated with a substance or element that imparts resistance to oxidation, such as a plating of gold or silver.

In some embodiments of a bipolar blade, the electrodes comprise three conductive layers spaced apart by intermediate electrical insulation layers, wherein the intermediate layer defines a peripheral edge portion of reduced cross-section (e.g., about 0.001 inches thick or less) for electrosurgical power or direct current power transmission. Such an intermediate layer may comprise a metal having a melting point of at least about 2600° F.

A heat sink structure may be included in various embodiments to establish a thermal gradient in the blade away from functional areas (i.e., by removing heat from the electrode). In an embodiment, the heat sink structure comprises a phase change material that changes from a first phase to a second phase upon absorption of thermal energy from the electrodes.

In various embodiments, the insulation is selected and fabricated so it has a surface free energy that reduces the propensity for electrosurgical decomposition products to stick to the surface. In some embodiments, at least the edge of the conductive element is composed of a material that reduces the propensity for electrosurgical decomposition products to stick to the surface and that is configured with a geometry that promotes the flow of thermal energy away from the edge when electrosurgical energy is being applied to tissue.

In the various embodiments, at least one electrically conductive element is electrically connected to an ESU. When connected to an ESU, RF current will flow from the electrically conductive element when contacting or in close proximity with an electrically conductive medium such as tissue or an electrically conductive liquid or vapor.

The various embodiments described generally above maybe understood by reference to the example embodiments illustrated in the figures, which will now be described in more detail.

Referring to FIG. 1, an electrically conductive element 1, which is typically metallic, can be surrounded by insulation 2. The conductive element 1 may be of any number of shapes, such as, but not limited to: substantially flat; having one or more curves; shaped as closed curves, such as rings or hoops; shaped as nonclosed curves, such as semicircles or crescents; planar; nonplanar, such as curved spatulas; having bends or curves, such as hooks; encompassing volumes, such as cups or cylindrical volumes; substantially blunt; having one or more regions that taper from one thickness to a lesser thickness; having opposing faces, such as forceps or scissors; and having one or more openings, such as holes, meshes, pores, or coils.

The conductive element 1 can have a tapered section 3. Additionally, the insulation 2 can have a tapered section 4. The combination of tapers on the conductive element 1 and the insulation 2 can produce bevels that transition down to the conductor edge 5. This leaves the conductor edge 5 exposed (i.e., not covered by insulation) so that electrical energy can transfer to tissue from the edge via conduction or capacitive electrical coupling, or both conduction and capacitive coupling, including with or without other energy transfer mechanisms that may be facilitated by an exposed edge including energy conveyed by conduction or radiation or a combination of conduction and radiation. The conductive element tapered section 3 provides a cross sectional profile that reduces the width of the conductive element 1 to form the conductor edge 5. The tapered section 3 may be reduced on one side of the profile or both, and may take on a variety of shapes as the width is reduced. For example, the cross sectional profile may include a radius of curvature that produces a concave profile, as illustrated in FIG. 1. As another example, the cross sectional profile may have a predominately flat profile, as illustrated in FIG. 5. Further, the cross sectional profile may have multiple radii of curvatures producing a cross sectional profile which combines concave and convex sections.

The conductor edge 5 is the portion of the conductive element 1 exposed from the insulation 2. In some embodiments, the conductor edge 5 is positioned at the edge of the blade. The conductor edge 5 is intended to be used in close proximity or touching tissue 6, as illustrated in FIG. 1. A narrow gap region 7 between the conductor edge 5 and tissue 6 is where electrosurgical energy interacts with tissue 6 via the transmission of electrosurgical energy.

In the blade configuration shown in FIG. 1, the outer profile of the tip end of the blade is approximately parabolic. As a result, in the vicinity of the conductor edge 5, the outer profile defined by the insulation 2 is relatively wide compared to the thickness of the conductor edge 5. This aspect of the blade is shown in more detail in FIG. 2.

FIG. 2 is a magnified view of the area around the narrow gap region 7 illustrated in FIG. 1. Shown are electrical conductive element 1, outer insulation 2, conductor edge 5, and tissue 6. Sparks and other means of electrosurgical energy transfer occur mostly in the primary reaction region 18, producing electrosurgical decomposition products which are depicted by the dashed arrows 19. The electrosurgical decomposition products 19 include gases, such as steam, entrained particles, and liquids that have been heated. The volume of electrosurgical decomposition products 19, particularly the gases, will increase local gas pressure in the region 18 that force the electrosurgical products out through the gap formed between the tissue 6 and the combination of the blade insulation 2 and conductor edge 5. For clarity, only one conductor is shown in FIGS. 1 and 2, whereas in various embodiments multiple electrodes may be present.

The flow of the electrosurgical decomposition products 19 away from the functional area may be inhibited by the viscous drag that results from the narrowness and length of the gap as well as the tortuousity of the path due to the roughness of the tissue, roughness of the blade, and contact between the tissue 6 and the insulation 2 or conductor edge 5. The more the flow of electrosurgical decomposition products 19 is inhibited, the greater the local pressure rise and the longer the reaction products remain exposed to high temperatures in the region 18. In use, tissue 6 which contacts the insulation 2 in the primary reaction region 18 may form temporary sealed pockets of gas, further inhibiting flow of reaction products. The inhibited flow from either viscous drag or temporarily sealed pockets is exacerbated when the blade is pressed into the tissue 6 by the user as a natural part of the surgical incision process. The result of these overall interactions is that the electrosurgical decomposition products in the gap region 18 between the tissue 6 and the insulation 2 and conductor edge 5 becomes pressurized to sufficient pressure to expel reaction products to achieve an approximate and temporary equilibrium between the rate of material forming and the rate of material leaving the region 18.

Even when the local pressure is high enough to force electrosurgical products from the primary reaction region 18, the resulting local temperature can be high enough to promote rapid pyrolysis and cause electropyrolysis to occur. A major constituent of many tissues is water. The conversion of water to steam is a significant absorber of energy when electrosurgical energy interacts with tissue. As a first approximation, the equilibrium temperature of saturated water and steam at the local pressure within the reactive region 18 can be used to estimate the minimum temperature that tissue in this region is exposed to during electrosurgery. For example, the estimated range of forces applied to blades by a user during an incision of tissue is about 0.15 N/mm to about 0.625 N/mm, where N/mm is Newtons per millimeter of blade movement through the tissue. If a blade has a blunt (approximately flat) profile facing the tissue (as is the case with the broad parabolic profile illustrated in FIG. 2) with a width of about 0.0508 mm (0.002 inches), then the pressure applied to the tissue when the applied force is 0.2 N/mm will be approximately 3.94 N/mm (3.94 MPA). At this pressure water boils to steam at about 250° C. (482° F.), a temperature that is high enough for tissue to pyrolyze and leave carbon-rich residues. Carbon-rich residues are those in which at least some of the electrosurgical decomposition products have a ratio of hydrogen atoms to carbon atoms less than about 1. Such carbon-rich residues are believed to be a major constituent of eschar.

The wider the contact surface in the primary reaction region 18, the greater the likelihood that tissue 6 will contact and momentarily stick to insulation 2 and the conductor edge 5, and thus, the greater the likelihood that materials will be sealed briefly in fixed volumes (e.g., pockets). As electrosurgical energy flows into a sealed volume within the reaction region 18, the equilibrium temperature will increase as pressure increases until the pressure reaches a point sufficiently high to burst through the seal of tissue stuck to the blade. Therefore, wide contact surfaces tend to lead to localized high pressure and high temperature regions as well as increase the time that electrosurgical decomposition products reside within the vicinity of the primary reaction region 18. Various embodiments use blade geometries that prevent local temperatures proximate to the conductor edge 5 from exceeding about 190° C. based upon saturated steam conditions and assuming an applied usage pressure of 0.2 N/mm. Some embodiments use blade geometries that limit the pressure on the edge of the blade to less than about 1.2 MPa.

Figure 3:
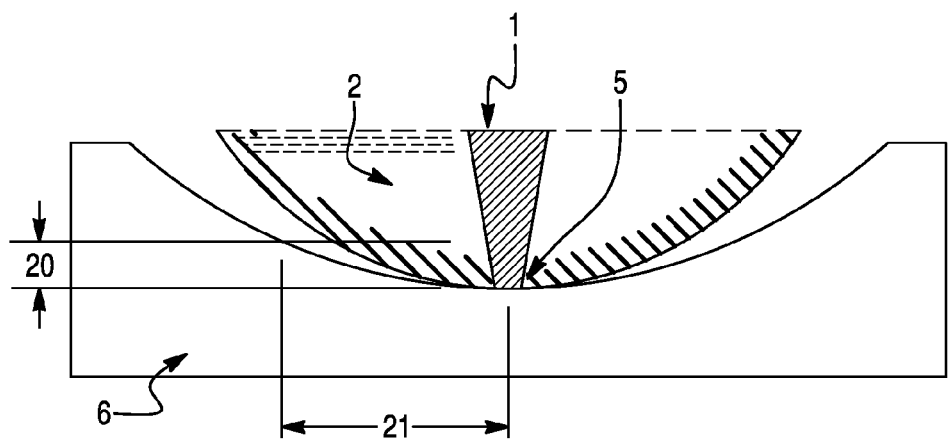
FIG. 3 portrays a magnified section of the region where electrosurgical energy interacts with tissue for the blade illustrated in FIG. 2 and shows the blade depth and half-width.

Referring to FIG. 3, some embodiments use blade geometries which include an edge depth 20 of about 0.254 mm (0.010 inches) with a blade edge half width 21 of less than about 0.5 mm (0.02 inches). In a further embodiment, the blade edge half width 21 is less than about 0.25 mm (~0.01 inches), and in yet another embodiment the blade edge half width 21 is less than about 0.12 mm (~0.005 inches).

Figure 6:
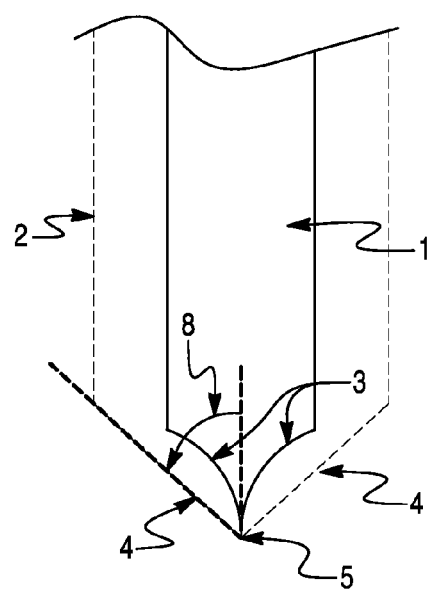
FIG. 6 portrays a cross-section of a blade with a conductive element that has a concave taper that has been insulated whereby the outer taper to the edge is not defined by a single smooth curve at the conductor edge and that shows the insulation angle.
Figure 8:
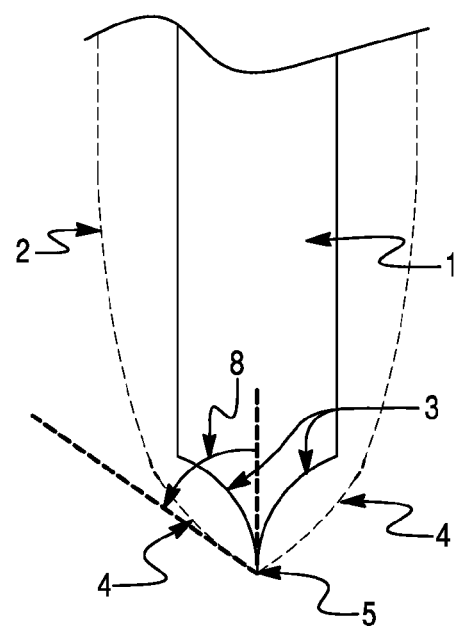
FIG. 8 portrays a cross-section of a blade with a conductive element that has a concave taper that has an overall profile that has a taper that transitions from curved to approximately flat at the edge of the blade.

To achieve reaction conditions that lead to reduced smoke and eschar, blade profiles can be used that are generally tapered in the vicinity of the edge conductor such that a tangent to the insulation at the conductor edge forms an acute angle 8 (i.e., less than 90 degrees) with the centerline of the blade as shown in FIGS. 6 and 8. Blade profiles with an acute insulation angle 8 are preferred over profiles that are of an approximately parabolic form as shown in FIG. 1. FIG. 4 and FIG. 5 illustrate geometries where the outer blade profile defined by insulation 2 is shaped with more than a single smooth curve and that join at the conductor edge 5.

FIG. 4 illustrates an embodiment where the conductive element 1 is surrounded by insulation 2 and the conductive element 1 has a concave taper 3 that results in a narrow conductor edge 5. In the embodiment illustrated in FIG. 4, the insulation 2 covering the conductive element 1 reduces in thickness toward the narrow edge until the conductive element metal is exposed forming the conductor edge 5. In this embodiment, the insulation 2 has an insulation taper 4 that also has a generally concave shape defined by the curves that smoothly terminate at the conductor edge 5. This geometry presents few opportunities for tissue to press against the edge of the blade to form seals or tortuous paths compared with the blade profile shown in FIG. 1.

FIG. 5 illustrates an embodiment similar to that shown in FIG. 4 except that the conductive element taper 3 and insulation taper 4 are approximately linear (i.e., flat) instead of being concave. As with the embodiment shown in FIG. 4, the geometry of the embodiment shown in FIG. 5 provides little opportunity for tissue to press against the edge of the blade and form seals or tortuous paths compared to the blade geometry shown in FIG. 1. Other embodiments include an insulation taper formed such that the surface of the insulation follows more than one curve defining the insulation taper in the vicinity of the conductor edge 5.

Figure 7:
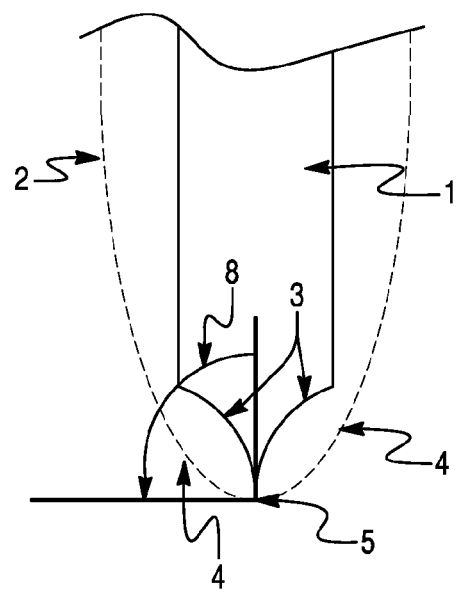
FIG. 7 portrays a cross-section of a blade with a conductive element where the outer taper to the edge is defined by a single smooth curve at the conductor edge showing the insulation angle.

FIG. 6 illustrates a blade embodiment that includes an acute insulation angle 8. The insulation angle is the angle formed between a line tangent to the insulation bevel 4 at the conductor edge 5 and a line parallel to the centerline of the blade edge 5. FIG. 7 illustrates the insulation angle 8 that occurs when the insulation taper 4 is be characterized by a single continuous smooth curve (a broad parabola in this case) compared to FIG. 6 where the insulation angle 8 that occurs is characterized by two curves (flat lines in this case) that essentially intersect at the conductor edge 5. FIG. 8 illustrates the case where the insulation 2 transitions from one curve to another before two separate curves intersect near the conductor tip 5 forming an acute insulation angle 8.

In the various embodiments, the insulation angle 8 should be less than 90 degrees, and preferably should be less than about 60 degrees, more preferably less than about 50 degrees, and still more preferably less than about 45 degrees.

Figure 9:
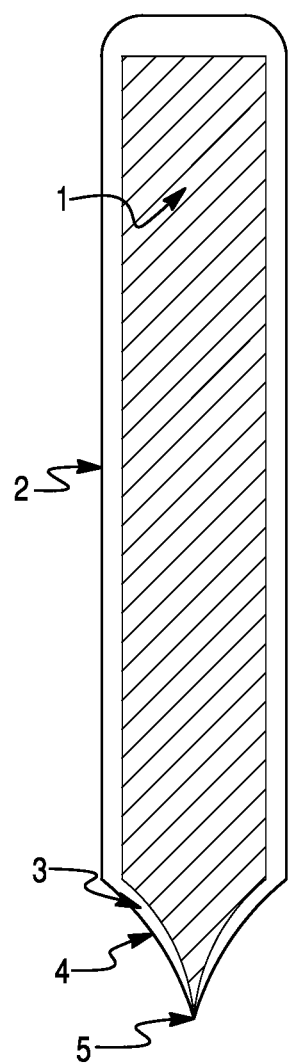
FIG. 9 portrays a cross section of a blade having a conductive element that has a concave taper and a concave overall taper to an edge.

A number of geometries for the taper portion can be employed to achieve an insulation angle of less than 90 degrees. FIG. 3 illustrates a narrow parabola geometry with an acute insulation angle. FIG. 4 illustrates a concave geometry which results in an acute insulation angle. FIGS. 5 and 6 illustrate a flat (i.e., linear) taper with an acute insulation angle. FIG. 8 illustrates a two-curve geometry resulting in an acute insulation angle. FIG. 9 illustrates a blade cross-section that has an insulation taper 4 that is concave. FIG. 9 also illustrates a conductive element 1 with a concave tapered region 3 that reduces down to form the conductor edge 5. Embodiments with conductive elements that have substantially concave tapers down to the edge facilitate the production of an outer insulation profile that is also concave as FIG. 9 illustrates.

The blade thickness profile embodiments illustrated in FIGS. 1-9 can be used for a cutting blade with a planar shape similar to a scalpel, in which case the width of the blade would extend out of the page. Additionally, thickness profile embodiments illustrated in FIGS. 1-9 can be used with a needle electrode, in which case the width extending out of the page would be approximately equal to the thickness profile, an example of which is illustrated in FIG. 14.

Restricting the amount of time that tissue and electrosurgical decomposition products are exposed to electrosurgical energy reduces the amount of eschar and smoke produced and reduces the amount of tissue damage. When the edge of blade contacts tissue for a period of time longer than is necessary to achieve the predetermined surgical effect, such as cutting, then more smoke and eschar are produced and more tissue damage occurs. The various embodiments include insulation 2 over the conductive element 1 which insulates the outside of the blade except for the exposed conductor edge 5, as has been illustrated in FIGS. 1-9. The insulation 2 restricts the flow of electrosurgical energy from the conductive element 1 to the tissue 6 except at the conductor edge 5. To serve this function, the insulation 2 needs to be of an adequate dimension so as to restrict or prevent the flow electrosurgical energy. However, too much insulation may make the blade width excessive.

The conductive element 1 both conveys electrical energy to the conductor edge 5 and conducts thermal energy away from the conductor edge 5 to help keep the blade relatively cool. Making the conductor edge 5 thick would facilitate conducting heat away from the edge, but if the edge is too thick then more sealing of tissue against the edge can occur with the coincident increase in smoke and eschar production and tissue damage. The ability of the conductive element 1 to remove thermal energy from the conductor edge 5 depends on the thermal conductivity of the material from which it is made. This relationship between thermal conductivity and the width of the edge can be expressed as the product of thermal conductivity and the width of the conductor edge 5, such that a poorer thermal conductor needs a wider path than a better thermal conductor. As used herein, the term "thermal path conductance" refers to the product of the conductive element material's thermal conductivity and the width of the thermal flow path, where the thermal conductivity is measured in W/m/° K at about 300 ° K and the width is measured in meters, leading to the units of thermal path conductance being W/° K. The various embodiments can have a thermal path conductance at the conductor edge of at least 0.0002 W/° K, preferably of at least 0.0003 W/° K, more preferably of at least 0.0006 W/° K, and still more preferably of at least 0.001 W/° K. For example, if the thermal path width is 0.0005 inches (1.27E-5 m) and the material used is molybdenum having a thermal conductivity of about 138 W/m/° K, then the thermal path conductance is about 0.00175 W/° K. In a blade having a planar configuration like a scalpel, the width of the thermal path will be the thickness of the blade at the edge.

To reduce the amount of tissue heated, the electrosurgical energy is focused in the various embodiments. One method of focusing the energy is to insulate the blade except for an exposed edge. Preferably, the exposed conductor edge 5 of the conductive element 1 is flush with the insulation layer 2 so as to avoid any recessed pockets and an unnecessarily broad reaction area such as formed if the electrode is recessed into a pocket in the insulation, the edge is coated with an insulator, or the edge is rounded. In some embodiments, the conductor edge 5 adjoins the insulating layer 2 to form a singular tapered exterior surface. Focusing electrosurgical energy is further facilitated by having a narrow conductor edge 5.

A flush, non-recessed conductor edge 5 further facilitates the electrosurgical process beyond the focus of electrosurgical energy. If the conductor edge is recessed within the insulation, then a pocket exists where tissue or electrosurgical decomposition products can accumulate and remain exposed for long durations to electrosurgical energy, thus promoting continued pyrolysis and electropyrolysis. In an embodiment, no pockets or recesses should exist where tissue or electrosurgical decomposition products can accumulate. Therefore, gaps or recesses between the conductor edge and the insulation are avoided in various embodiments. By adjoining the conductor edge with the insulating layer to form a flush exterior tapered surface with no gaps or recesses, the singular exterior tapered surface can take on a strictly convex shape immediately adjacent to the conductor edge. This embodiment reduces or eliminates opportunities for trapping tissue during use. Away from the conductor edge the profile of the insulation taper can be concave. This embodiment reduces residency time at high temperatures and reduces pressure which reduces the equilibrium steam temperature.

In addition to avoiding gaps or recess between the conductor edge 5 and the insulation layer 2, the conductor edge 5 itself should not have recesses in the conductive element material that might promote the trapping of tissue or electrosurgical decomposition products. Preferably the conductor edge 5 is relatively smooth and does not have recesses along its length or width, such sawtooth, gaps, pockets or holes that are larger than about 32 microinches.

Embodiments of the invention include conductor edge shapes that are pointed, terminate to an acute angle, or are flat. Preferably, the shape of the conductor edge 5 is not rounded. Preferably the conductor edge has a thickness less than about 0.005 inches, more preferably less than about 0.002 inches, more preferably less than about 0.001 inches, and even more preferably about 0.0005 inches or less.

The thickness of the insulation layer, particularly at the area proximate to the conductor edge, affects the overall thickness of the edge of the blade. Enough insulation needs to be present to restrict the rate of energy transfer out the sides of the blade into tissue or electrosurgical decomposition products to prevent or reduce continued changes in those materials. Restricting the rate of energy transfer out the sides is particularly important near the conductor edge where temperatures will be highest. If the insulation is thicker than necessary to prevent continued changes in tissue or electrosurgical decomposition products, then the blade will be wider than necessary near the conductor edge, which increases the opportunities for sealing tissue against the conductor edge or the insulation near the conductor edge.

When conductive element 1 is tapered so that it is thinnest at the conductor edge 5, as illustrated in FIGS. 1-9, the temperature of the conductive element will decrease as the distance from the conductor edge 5 increases. Therefore, the thickest insulation needs to be near the conductor edge 5, allowing the shape of the insulation 2 to have a tapered region 4 that needs to be no thicker than it is near the conductor edge 5. The thickness of the insulation at the conductor edge can be at least one half of the thickness of the conductor edge and more preferably at least equal to about the thickness of the conductor edge. For example, if the conductor edge can have a thickness of 0.001 inches then the insulation surrounding the conductor edge preferably has a thickness of about 0.0005 inches and preferably has a thickness of about 0.001 inches.

The main portion of the conductive element 1 should be thick enough to readily conduct heat away from the conductor edge 5. The width of the conductive element 1 can have a thickness before the taper portion 3 that is at least about 5 times as thick as the conductor edge 5, preferably at least about 10 times as thick as the conductor edge 5, and more preferably at least about 20 times as thick as the conductor edge 5. For example, if the conductor edge is 0.001 inches thick and the conductive element thickness before the taper begins is 0.020 inches, then the ratio of the thickness of the conductive element to the thickness of the conductor edge is 20.

In addition to the edge geometry, the overall configuration of the blade contributes the generation of excessive decomposition products and increased tissue damage. For example, FIG. 10 illustrates a blade connected to shaft 11 that has blade body 10 with intersecting conductor edges 13 that subtend intersecting edge angle 14. In use, the blade produces the predetermined surgical effect (e.g., cutting) when the blade is moved through tissue in the direction indicated by arrow 12. This blade configuration moving through tissue 6 is illustrated in FIG. 11. As the blade 10 moves through tissue, an electrosurgically affected tissue region 16 is created. As the blade 10 moves through tissue 6, the leading corner 13b initially contacts the tissue near the bottom of the blade and bottom edge 13a then continues to supply electrosurgical energy to the already affected tissue as the blade is moved. Thus, the bottom conductor edge 13a prolongs the residence time that the tissue along bottom conductor edge 13a is affected by electrosurgical energy. The prolonged residence time increases smoke and eschar production and increases tissue damage. The intersecting edge angle 14 influences whether such prolonged residence time occurs and the closer that the angle is to 180 degrees (i.e., the less there is a trailing edge) the less likely that prolonged residence time occurs. If the intersecting edge angle 14 is made more acute, the situation depicted in FIG. 12 occurs. While the residence time of tissue near the trailing edge 15 is reduced in the configuration illustrated in FIG. 12, the trailing conductor edge 15 following the incision does continue supplying electrosurgical energy to tissue 16 that has already been affected by electrosurgical energy delivered from the leading edge 13.

Figure 12:
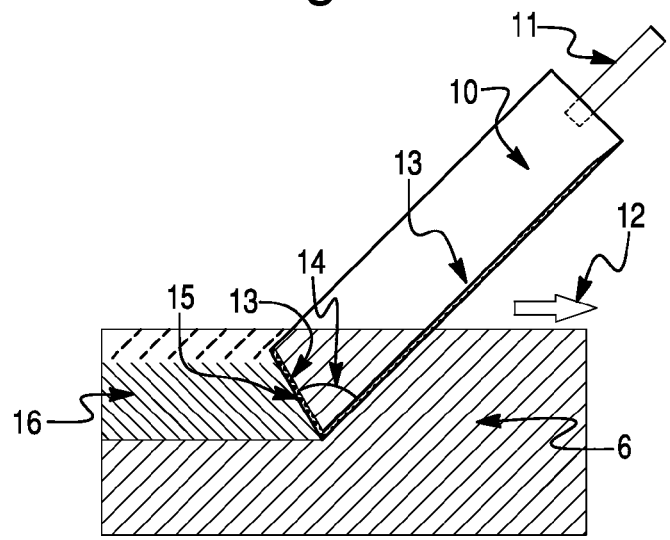
FIG. 12 portrays a side view of blade with two exposed edges at an acute angle in relation to making a tissue incision.

The intersecting conductor edges 13 in FIGS. 10-12 provide a point of concentration for electrosurgical energy when the blade first contacts tissue 6 facilitating starting an electrosurgical effect such as cutting. Thus, such a concentration is desirable because it makes starting or controlling the electrosurgical effect easier. In various embodiments, the intersecting conductor edges angle does not allow the blade to be oriented during use such that tissue is exposed to an active edge (and thus exposed to electrosurgical energy) for a prolonged residence time. In some embodiments, the intersecting edge angle is obtuse, in some embodiments the intersecting edge angle is greater than about 160 degrees, and in an embodiment the intersecting edge angle is approximately equal to about 180 degrees. The example embodiment geometries illustrated in the figures show edges that are substantially straight. Other embodiments include edges that have one or more curves, such as edges comprised of one or more parts of ellipses, circles, parabolas, or hyperbolas, and edges composed of a multiplicity of straight sections as well as edges composed of one or more combinations of straight sections and curves.

In an embodiment, only one conductor edge is present as illustrated in FIG. 13. The single conductor edge 13 is also the leading edge 13c that first transfers electrosurgical energy to tissue 6 producing the electrosurgically affected tissue region 16. The trailing edge 13d is not a functional surface, i.e., it does not transfer electrosurgical energy to tissue because it does not have an exposed surface (conductor edge) capable of transferring electrosurgical energy to tissue. The blade illustrated in FIG. 13 comes to a region 13e where electrosurgical energy is concentrated when the blade first contacts tissue 6.

In an embodiment the width of the blade is made sufficiently short so that the blade comes to a point without an edge, such as illustrated in FIG. 14. In this embodiment, the point 17 may have a substantially (though not necessarily) circular cross-section as it tapers from the body 10 to the tip 17. This embodiment is referred to herein as a needle electrode since its width is approximately equal to its thickness; however, its cross section may be oblong, oval, square or other shape in addition to, or instead of, circular and may be comprised of one or more curves or portions of curves such as ellipses, parabolas, or hyperbolas, possibly in conjunction with one or more substantially straight sections or may be comprised of a multiplicity of straight segments forming a polygon, not necessarily a regular polygon. This profile need not necessarily be strictly convex. Also, the profile may have one or more openings or crevices passing at least partially along the length of the needle.

In various embodiments, the blade has one or more conductor edges configured so that they cause electrosurgical energy to enter tissue only at the time when the blade first encounters tissue that has not yet experienced the predetermined electrosurgical effect. In some embodiments, the blade has one or more conductor edges configured so that they have a region that concentrates electrosurgical energy when the blade first contacts tissue, such as in a region that approximates a point, and such blade has one or more conductor edges configured so that they cause electrosurgical energy to enter tissue only at the time when the blade first encounters tissue that has not yet had the predetermined electrosurgical affect occur. For embodiments where the blade is to be used as a scalpel for cutting and other electrosurgical functions, the embodiments may have a single conductor edge that comes to a point approximately.

By employing various embodiments, a higher crest factor electrosurgical energy can be used for the predetermined surgical effect of cutting without excessive damage to tissue or generation of smoke or eschar. Crest factor is the ratio of peak voltage to the RMS voltage. During cutting, crest factors of less than about 5 and typically less than about 3 are used. For a predetermined surgical effect of moderate coagulation crest factors of about 4 to 5 are typically used. To achieve the predetermined surgical effect of aggressive coagulation, crest factors greater than 8, typically of about 9, are used. If cutting tissue is attempted with conventional blades and crest factors that are too high, the cutting effect will be very poor and blades that do not incorporate features of the various embodiments will immediately accumulate large masses of adherent tissue that prevents further use until the blade is cleaned. Moreover, at a crest factor of about 8 ordinary electrosurgical blades do not cut at all or very poorly. Thus, the drawbacks of conventional electrosurgical blades prevent the use of high crest factors for cutting. By focusing electrosurgical energy and reducing the residence time during which tissue is exposed to electrosurgical energy the various embodiments of the present invention allow use of higher crest factors for cutting.

Using high crest factors for cutting enhances hemostasis. Enhancing hemostasis is particularly beneficial when the tissue being affected is highly vascularized, such as the liver.

One embodiment provides a blade that cuts with enhanced hemostasis that comprises an insulated conductive element that tapers to one or more conductor edges that are at least partially exposed such that they can transfer electrosurgical energy to tissue and that have thermal path conductance that is at least 0.0002 W/° K, wherein the exposed edge is no thicker than about 0.005 inches and the blade is connected to an ESU configured to supply electrosurgical power with a crest factor of about 5 or larger. An embodiment provides a blade that cuts with the ESU configured to supply electrosurgical power with a crest factor of about 8 or larger.

In an embodiment, a method of using an electrosurgical instrument includes connecting an electrosurgical instrument having a blade configured according to various embodiments to an ESU, adjusting the ESU to output RF power with a wave form (i.e., shape of the RF power versus time) having a crest factor of about 5 or higher, and bringing the electrosurgical instrument close to or in contact with tissue to make an incision or conduct a cutting procedure (i.e., the predetermined electrosurgical effect includes cutting tissue). In another embodiment, a method of using an electrosurgical instrument includes connecting an electrosurgical instrument having a blade configured according to various embodiments to an ESU, adjusting the ESU to output RF power with a wave form having a crest factor of about 8 or higher, and bringing the electrosurgical instrument close to or in contact with tissue to make an incision or conduct a cutting procedure.

In various embodiments, the outer insulating layer may have a maximum thermal conductance of about 1.2 W/cm$^2$ ° K when measured at about 300 ° K, preferably about 0.12 W/cm$^2$ ° K or less when measured at about 300 ° K, and more preferably about 0.03 W/cm$^2$ ° K when measured at about 300 ° K. As used herein, thermal conductance refers to a measure of the overall thermal transfer across any given cross section (e.g. of the insulation layer), taking into account both the thermal conductivity of the materials comprising such layer and the thickness of the layer (i.e. thermal conductance of layer=thermal conductivity of material comprising the layer (W/cm ° K)/thickness of the layer (cm)).

In relation to the various embodiments, the insulation layer should also exhibit a dielectric withstand voltage of at least the peak-to-peak voltages that may be experienced by the electrosurgical instrument during surgical procedures. The peak voltages will depend upon the settings of the RF source employed, as may be selected by clinicians for particular surgical procedures. In various embodiments, the insulation layer should exhibit a dielectric withstand voltage of at least about 50 volts, and more preferably, at least about 150 volts. As used herein, the term "dielectric withstand voltage" means the capability to avoid an electrical breakdown (e.g. an electrical discharge through the insulating layer) for electrical potentials up to the specified voltage.

In some embodiments, the insulating or electrode bonding layer may comprise a porous ceramic material that has had at least the pores on the surface sealed to prevent or impede the penetration of biological materials into the pores. Such ceramic may be applied to the electrodes via dipping, spraying, etc., followed by curing via drying, firing, etc. Preferably, the ceramic insulating layer should be able to withstand temperatures of at least about 2000° F.

The ceramic insulating layer may comprise various metal/non-metal combinations, including for example compositions that comprise the following: aluminum oxides (e.g. alumina and $Al_2O_3$), zirconium oxides (e.g. $Zr_2O_3$), zirconium nitrides (e.g. ZrN), zirconium carbides (e.g. ZrC), boron carbides (e.g. $B_4C$), silicon oxides (e.g. $SiO_2$), mica, magnesium-zirconium oxides (e.g. $(Mg-Zr)O_3$), zirconium-silicon oxides (e.g. $(Zr-Si)O_2$), titanium oxides (e.g., $TiO_2$) tantalum oxides (e.g. $Ta_2O_5$), tantalum nitrides (e.g. TaN), tantalum carbides (e.g., TaC), silicon nitrides (e.g. $Si_3N_4$), silicon carbides (e.g. SiC), tungsten carbides (e.g. WC) titanium nitrides (e.g. TiN), titanium carbides (e.g., TiC), niobium nitrides (e.g. NbN), niobium carbides (e.g. NbC), vanadium nitrides (e.g. VN), vanadium carbides (e.g. VC), and hydroxyapatite (e.g. substances containing compounds such as $3Ca_3(PO_4)_2Ca(OH)_2Ca_{10}(PO_4)_6(OH)_2Ca_5(OH)(PO_4)_3$, and $Ca_{10}H_2O_{26}P_6$). One or more ceramic layers may be employed, wherein one or more layers may be porous, such as holes filled with one or more gases or vapors. Such porous compositions will usually have lower thermal conductivity than nonporous materials. An example of such materials is foam, such as an open cell silicon carbide foam. Such porous materials have the disadvantage that they allow fluids, vapors, or solids to enter the pores whereby they are exposed to prolonged contact with high temperatures which can lead to thermal decomposition or oxidation and produce smoke or other noxious or possibly dangerous materials. Sealing the surface of the ceramic prevents such incursions, while substantially preserving the beneficial reduced thermal conductivity of the pores.

Ceramic coatings or electrode bonding materials may also be formed in whole or part from preceramic polymers that when heated form materials containing Si—O bonds able to resist decomposition when exposed to temperatures in excess of 1200° F., including compositions that use one or more of the following as preceramic polymers: silazanes, polysilazanes, polyalkoxysilanes, polyureasilazane, diorganosilanes, polydiorganosilanes, silanes, polysilanes, silanols, siloxanes, polysiloxanes, silsesquioxanes, polymethylsilsesquioxane, polyphenyl-propylsilsesquioxane, polyphenylsilsesquioxane, polyphenyl-vinylsilsesquioxane. Preceramic polymers may be used to form the ceramic coating by themselves or with the addition of inorganic fillers such as clays or fibers, including those that contain silicon oxide, aluminum oxides, magnesium oxides, titanium oxides, chrome oxides, calcium oxides, or zirconium oxides.

Ceramic coatings may also be formed by mixing one or more colloidal silicate solutions with one or more filler materials such as one or more fibers or clays. The filler materials can contain one or more materials that have at least 30 percent by weight $Al_2O_3$ or $SiO_2$ either alone or combined with other elements, such occurs in kaolin or talc. The colloidal silicate and filler mixture may optionally contain other substances to improve adhesion to electrode surfaces or promote producing a sealed or hydrophobic surface. Representative examples of colloidal silicate solutions are alkali metal silicates, including those of lithium polysilicate, sodium silicate, and potassium silicate, and colloidal silica. Fibers may include those that contain in part or wholly alumina or silica or calcium silicate, and Wollastonite. Clays may include those substances that are members of the smectite group of phyllosilicate minerals. Representative examples of clay minerals include bentonite, talc, kaolin (kaolinite), mica, clay, sericite, hectorite, montmorillonite and smectite. Various embodiments use at least one of kaolin, talc, and montmorillonite. These clay minerals can be used singly or in combination. In various embodiments, at least one dimension, such as diameter or particle size, of at least one of the filler materials has a mean value of less than 200 micrometers and more preferably has a mean value of less than 50 micrometers and even more preferably has a mean value of less than 10 microns and still more preferably has a mean value less than 5 microns Substances that may be added to promote adhesion or production of a sealed or hydrophobic surface include those that increase the pH of the mixture, including sodium hydroxide or potassium hydroxide, and hydrolysable silanes that condense to form one or more cross-linked silicone-oxygen-silicon structures.

Sealing a porous insulator is accomplished not by coating the ceramic in the sense that electrosurgical accessories have been coated with PTFE, silicone polymers and other such materials. Best surgical performance occurs when accessories are thin, therefore pores are best filled by a material that penetrates the surface of the porous material and seals the pores. Some residual material may remain on the surface, but such material is incidental to the sealing process.

Sealing materials need to withstand temperatures exceeding 400° F. and more preferably withstand temperatures exceeding 600° F. Silicates and solutions containing or forming silicates upon curing can be used. Other materials may be used, including silicone and fluorosilicones. For sealing, the materials need to have low viscosity and other properties that enable penetration into the surface of the porous insulator. Traditional silicone and fluorosilicone polymer-forming compounds do not have these properties unless they are extensively diluted with a thinning agent, such as xylene or acetone.

A sealed porous insulation may be employed to yield an average maximum thermal conductivity of about 0.006 W/cm-° K or less where measured at 300 ° K. The insulating layer outside of the blade can have a thickness of between about 0.001 and 0.2 inches, and preferably between about 0.005 and 0.100 inches and more preferably between about 0.005 and 0.050 inches.

A coating that is applied as a single substance that upon curing does not require sealing may also be used for the outer insulation or as the bonding material between electrodes. Examples of such coatings include those formed from mixtures that use one or more of the aforementioned colloidal silicates and clays and also use one or more substances that reduce the surface free energy of the surface. Substances that reduce the surface free energy include: halogenated compounds, fluoropolymer compounds, such as PTFE and PFA, including aqueous dispersions of such compounds; and organofunctional hydrolysable silanes, including those containing one or more fluorine atoms on one or more pendant carbon chains.

In some embodiments, a hydrolysable silane is a component in the coating or in the insulating material between electrodes, with the hydrolysable silane having one or more halogen atoms and having a general formula of $CF_3(CF_2)_m(CH2)_nSi(OCH_2CH_3)_3$ where m is preferably less about 20 and more preferably about 5 or less and where n is preferably about 2. Other groups besides $(OCH_2CH_3)_3$, such as those based on ethyl groups, may be used and fall within the scope of the various embodiments when they also are hydrolysable. Other halogens, such as chlorine, may be substituted for the fluorine, although these will typically produce inferior results.

Preferably, the surface energy (also referred to as the surface tension or the surface free energy) of the coating is less than about 32 millinewtons/meter and more preferably less than about 25 millinewtons/meter and even more preferably less than about 15 millinewtons/meter and yet more preferably less than about 10 millinewtons/meter.

In an embodiment, the conductive elements or conductor edges or both of the electrosurgical instrument may be configured to have a thermal conductivity of at least about 0.35 W/cm ° K when measured at about 300 ° K. By way of example, the conductive elements or conductor edges or both may comprise at least one metal selected from the group including: silver, copper, aluminum, gold, tungsten, tantalum, columbium (i.e., niobium), and molybdenum. Alloys comprising at least about 50% (by weight) of such metals may be employed, and even more preferably at least about 90% (by weight). Additional metals that may be employed in such alloys include zinc.

In various embodiments, at least a portion of the conductor edge is not insulated (i.e. not covered by the outer insulating layer). In connection therewith, when the conductor edge comprises copper, the exposed portion may be coated or plated (e.g. about 10 microns or less) with a biocompatible metal. By way of example, such biocompatible metal may be selected from the group including: nickel, silver, gold, chrome, titanium tungsten, tantalum, columbium (i.e., niobium), and molybdenum.

In some embodiments, the conductive element, conductor edge, or both may comprise two or more layers of different materials. More particularly, at least a first metal layer may be provided to define at least part of the conductor edge that is functional to convey electrosurgical energy to tissue as described above. Such first metal layer may comprise a metal having a melting temperature greater than about 2600° F., preferably greater than about 3000° F., and more preferably greater than about 4000° F., thereby enhancing the maintenance of a desired peripheral edge thickness during use (e.g. the outer extreme edge noted above). Further, the first metal layer may have a thermal conductivity of at least about 0.35 W/cm ° K when measured at 300 ° K.

For living human/animal applications, the first metal layer may comprise a first material selected from a group including: tungsten, tantalum, columbium (i.e., niobium), and molybdenum. All of these metals have thermal conductivities within the range of about 0.5 to 1.65 W/cm ° K when measured at 300 ° K. Alloys comprising at least about 50% by weight of at least one of the group of materials may be employed, and more preferably at least about 90% by weight.

In addition to the first metal layer, the conductive element may further comprise at least one second metal layer on the top and/or bottom of the first metal layer. A first metal layer as noted above can be provided in a laminate arrangement between top and bottom second metal layers. To provide for rapid heat removal, the second metal layer(s) preferably has a thermal conductivity of at least about 2 W/cm ° K. By way of example, the second layer(s) may advantageously comprise a second material selected from the group including: copper, gold, silver and aluminum. Alloys comprising at least about 50% of such materials may be employed, and more preferably at least about 90% by weight. It is also preferable that the thickness of the first metal layer and of each second metal layer (e.g. for each of a top and bottom layer) be between about 0.001 and 0.25 inches, and even more preferably between about 0.005 and 0.1 inches.

One or more of the conductor edges may be plated with gold or silver or alloys thereof to confer added oxidation resistance to the portions of the electrodes exposed to tissue or current flow or both. Such plating may be applied using electroplating, roll-bonding or other means either after assembly or prior to assembly of the electrodes to form blades. The plating thickness can be at least about 0.5 micrometers and preferably at least about 1 micrometer.

As may be appreciated, multi-layered metal bodies of the type described above may be formed using a variety of methods. By way of example, sheets of the first and second materials may be roll-bonded together then cut to size. Further, processes that employ heat or combinations of heat and pressure may also be utilized to yield a laminated electrode.

In some embodiments, the electrosurgical instrument may further comprise a heat sink for removing thermal energy from the conductor edge, conductive element, or both. In this regard, the provision of a heat sink helps establishes a thermal gradient for conducting heat away from the conductor edge, thereby reducing undesired thermal transfer to a tissue site. More particularly, it is preferable for the heat sink to operate so as to maintain the maximum temperature on the outside surface of the insulating layer at about 160° C. or less, more preferably at about 80° C. or less, and most preferably at 60° C. or less. Relatedly, it is preferable for the heat sink to operate to maintain an average conductive element temperature of about 500° C. or less, more preferably of about 200° C. or less, and most preferable of about 100° C. or less.

In an embodiment, the heat sink may comprise a vessel including a phase change material that either directly contacts a portion of the electrodes (e.g. a support shaft portion) or that contacts a metal interface provided on the vessel which is in turn in direct contact with a portion of the electrodes (e.g. a support shaft portion). Such phase change material changes from a first phase to a second phase upon absorption of thermal energy from the electrodes. In this regard, the phase change temperature for the material selected should preferably be greater than the room temperature at the operating environment and sufficiently great as to not change other than as a consequence of thermal heating of the electrosurgical instrument during use. Such phase change temperature should preferably be greater than about 30° C. and most preferably at least about 40° C. Further, the phase change temperature should be less than about 225° C. Most preferably, the phase change temperature should be less than about 85° C.

The phase change may be either from solid to liquid (i.e., the phase change is melting) or from liquid to vapor (i.e., the phase change is vaporization) or from solid to vapor (i.e., the phase change is sublimation). More practical phase changes to employ are melting and vaporization. By way of example, such a phase change material may comprise a material that is an organic substance (e.g., fatty acids, such as stearic acid, hydrocarbons such as paraffins) or an inorganic substance (e.g., water and water compounds containing sodium, such as, sodium silicate (2-)-5-water, sodium sulfate-10-water).

In an embodiment, the heat sink may comprise a gas flow stream that passes in direct contact with at least a portion of the electrodes. Such portion may be a peripheral edge portion and/or a shaft portion of the electrodes that is designed for supportive interface with a holder for hand-held use. Alternatively, such portion may be interior to at least a portion of the electrodes, such as interior to the exposed peripheral edge portion and/or the shaft portion of the electrodes that is designed for supportive interface with a holder for hand-held use. In yet other embodiments, the heat sink may simply comprise a thermal mass (e.g. disposed in a holder).

In an embodiment, an electrosurgical instrument comprises a main body portion having a blade-like configuration at a first end and an integral, approximately cylindrical shaft at a second end. The main body may comprise a highly-conductive metal and/or multiple metal layers as noted. At least a portion of the flattened blade end of the main body can be coated with a ceramic-based and/or silicon-based, polymer insulating layer, except for the peripheral edge portion thereof. The cylindrical shaft of the main body can be designed to fit within an outer holder that can be adapted for hand-held use by medical personnel. Such holder may also include a chamber comprising a phase-change material or other heat sink as noted hereinabove. Additionally, one or more control elements, such as buttons or switches, may be incorporated into the holder for selectively controlling power or other aspects of the device's operation, such as the application of one or more, predetermined, electrosurgical signal(s) from an RF energy source to the blade via the shaft of the main body portion.

In some embodiments, the conductive element 1 with its surrounding insulation 2 are provided as a single use sterile disposable blade that can be coupled to a holder or handle which may be reusable or a single use device. In such embodiments, the conductive element 1 includes electrical connector surfaces on the end proximal end (i.e., the end of the electrodes closest to the handle in use) suitable for electrically connecting to compatible electrical connector surfaces, such as a sleeve within the holder. The connector surfaces may also serve as a mechanical coupling so that by inserting the blade into the holder connector, the blade is rigidly held by the holder. In such embodiments, the reusable holder or handle may include one or more control components, such as buttons or switches, for selectively controlling power or other aspects of the device's operation, such as controlling the application of one or more, predetermined, electrosurgical signal(s) from an RF energy source to the blade via the shaft of the main body portion. In such an embodiment, a single use sterile disposable blade can be sealed in a sterile package, which may a single use dipsolable handle and/or include instructions for assembly and use, to provide an electrosurgical kit to be opened at the time surgery is to be performed.

Figure 15:
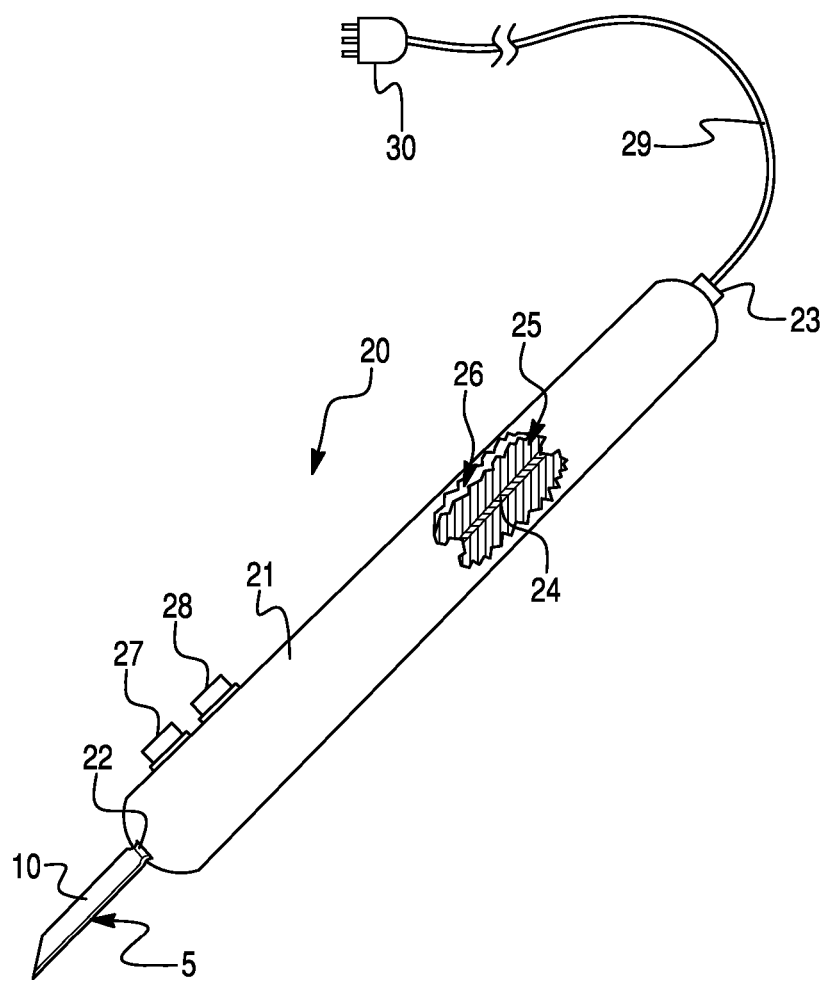
FIG. 15 illustrates an electrosurgical instrument including a holder and blade according to an embodiment.

In some embodiments, the conductive element 1 with its surrounding insulation 2 is fixedly coupled to a holder or handle 21 as a single use electrosurgical assembly 20, such as illustrated in FIG. 15. In such embodiments, the electrosurgical assembly 20 includes a blade 10 mechanically and electrically coupled to the holder or handle 21, such as by a connector 22. An electrical connector 23 on the holder or handle 21 can be provided to connect, such as by means of a cable 29, to an ESU or similar source of radio frequency (RF) AC power. An internal conductor 24 conducts the RF power from the connector 23 at one end of the handle 21 to the blade 10 at the other end of the handle 21. Electrical and thermal insulation 25 can be provided to isolate power being conducted in the internal conductor 24 from the holder exterior 26, thereby protecting the clinician using the electrosurgical assembly 20. The blade connector 22 may also include electrical insulation to electrically isolate the blade 10 from the handle exterior 26. Control elements 27, 28 may be provided on the handle 21 to enable a user to activate, deactivate and otherwise control power provided by the ESU or RF power source. The handle 21 may be shaped to enable a user to comfortably hold or otherwise manipulate the assembly 20, provided with a surface material or surface texture, such as roughening, to enhance a user's grip and other ergonomic features to aid a clinician in manipulating the disposable electrosurgical assembly 20. The handle 21 may be reusable or a single use disposable device. A cable 29 connectable to the connector 23 and fitted with a suitable electrical plug 30 can be used to electrically couple the handle 21 to the ESU. The cable 29 may be reusable or disposable. In an embodiment, the cable 29 and plug 30 are included as part of the electrosurgical assembly 20. In an embodiment including one or more control elements 27, 28 on the holder or handle 21, electronic connectors may be provided within cable 29 for relaying control signals to the ESU.

In some embodiments, the a single use sterile electrosurgical assembly 20 can be sealed in a sterile package, which may include a cable 29 and/or instructions for assembly and use, to provide an electrosurgical kit to be opened at the time surgery is to be performed.

Conventional electrosurgical signals may be advantageously employed in combination with one or more of the above-noted electrosurgical instrument embodiments. In particular, the inventive electrosurgical instrument yields benefits when employed with electrosurgical signals and associated apparatus of the type described in U.S. Pat. No. 6,074,387, hereby incorporated by reference in its entirety.

The apparatus and methods for reducing smoke, eschar, and tissue damage according to various embodiments may be applied in conjunction with other methods for reducing the local heating that promotes the excessive electrosurgical tissue decomposition which leads to smoke, eschar, and tissue damage. Such additional methods for reducing local heating include providing for an effective level of heat removal away from functional portions of an electrosurgical instrument and/or by otherwise enhancing the localized delivery of an electrosurgical signal to a tissue site, such as by reducing the exposed areas of either or both functional and nonfunctional areas by using thermal insulation.

While the present invention has been disclosed with reference to certain preferred embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

We claim:

1. A method for performing electro surgery to achieve a predetermined electro surgical effect on tissue, comprising:
    applying radiofrequency power having a crest factor of about 5 or greater to an electro surgical instrument comprising:
        an electrically conductive element having a first section and a first tapered section, wherein the first tapered section includes a beveled surface having a biconcave shape terminating at a conductor cutting edge, and
        an insulation layer having a second tapered section, wherein the second tapered section has a biconcave shape generally following the contours of and overlaying the biconcave shape of the first tapered section and tapering to expose the conductor cutting edge forming a primary reaction region at the conductor cutting edge; and
    positioning the electro surgical instrument near tissue.

2. The method for performing electrosurgery according to claim 1, wherein the applied radiofrequency power has a crest factor of about 8 or higher.

3. The method for performing electro surgery according to claim 1, further comprising performing an incision in the tissue using the electrosurgical instrument.

4. A method for performing electrosurgery to achieve a predetermined electro surgical effect on tissue, comprising:
    connecting a source of radio frequency power to an electro surgical instrument comprising:
        an electrically conductive element having a first section and a first tapered section terminating at a conductor edge, wherein the first tapered section includes a beveled surface having a concave shape, and
        an insulation layer having a second tapered section overlaying the conductive element which tapers against a side of the first tapered section to expose the conductor edge forming a primary reaction region, wherein the second tapered section has a concave shape;
    adjusting the source of radio frequency power to output a wave form having a crest factor equal to or greater than about 5;
    positioning the electrosurgical instrument near tissue; and
    cutting the tissue using the electrosurgical instrument.

5. The method for performing electrosurgery according to claim 4, wherein the source of radio frequency power is adjusted to output a wave form having a crest factor equal to or greater than about 8.

6. The method for performing electrosurgery according to claim 4, wherein the concave shape of the first tapered section is biconcave.

7. The method for performing electro surgery according to claim 4, wherein the concave shape of the second tapered section is biconcave-shape.

8. The method for performing electro surgery according to claim 4, wherein the second tapered section generally follows the contours of the first tapered section.

\* \* \* \* \*